(12) United States Patent
Giniger

(10) Patent No.: US 10,653,596 B2
(45) Date of Patent: May 19, 2020

(54) WHITE CHARCOAL TOOTHPASTE COMPOSITION AND METHOD

(71) Applicant: TOTAL CLEAN HOLDINGS LLC, New York, NY (US)

(72) Inventor: Martin Giniger, Delray Beach, FL (US)

(73) Assignee: TOTAL CLEAN HOLDINGS LLC, New York, NY (US)

( * ) Notice: Subject to any disclaimer, the term of this patent is extended or adjusted under 35 U.S.C. 154(b) by 49 days.

(21) Appl. No.: 16/217,401

(22) Filed: Dec. 12, 2018

(65) Prior Publication Data

US 2019/0247289 A1 Aug. 15, 2019

Related U.S. Application Data

(60) Provisional application No. 62/630,033, filed on Feb. 13, 2018.

(51) Int. Cl.
| | |
|---|---|
| *A61K 8/22* | (2006.01) |
| *A61K 8/25* | (2006.01) |
| *A61K 8/34* | (2006.01) |
| *A61K 8/46* | (2006.01) |
| *A61K 8/92* | (2006.01) |
| *A61K 8/29* | (2006.01) |
| *A61Q 11/00* | (2006.01) |
| *A61K 8/60* | (2006.01) |
| *A61K 8/97* | (2017.01) |

(52) U.S. Cl.
CPC ............ *A61K 8/22* (2013.01); *A61K 8/25* (2013.01); *A61K 8/29* (2013.01); *A61K 8/345* (2013.01); *A61K 8/463* (2013.01); *A61K 8/60* (2013.01); *A61K 8/922* (2013.01); *A61K 8/97* (2013.01); *A61Q 11/00* (2013.01); *A61K 2800/43* (2013.01); *A61K 2800/48* (2013.01); *A61K 2800/805* (2013.01)

(58) Field of Classification Search
None
See application file for complete search history.

(56) References Cited

U.S. PATENT DOCUMENTS

| | | |
|---|---|---|
| 3,538,230 A | 11/1970 | Pader et al. |
| 3,862,307 A | 1/1975 | Di Giulio |
| 4,181,712 A | 1/1980 | Rialdi |

*Primary Examiner* — Nannette Holloman
(74) *Attorney, Agent, or Firm* — Robert M Cox, Esq

(57) ABSTRACT

The present invention relates to a method of producing white activated charcoal (having a white-to-light-grey appearance) employing high temperatures and a hydrogen peroxide solution. The present invention further relates to one or more oral care compositions utilizing white activated charcoal, including a whitening toothpaste compound minimally comprising white activated charcoal and a dental abrasive in a solvent base. The present invention further relates to a highly effective whitening toothpaste compound further comprising one or more of: a humectant, a thickener, a foaming agent, a protective surface polish, an extrinsic stain remover, a sweetener, a flavoring and a white colorant—a complete whitening, polishing and cleaning toothpaste.

35 Claims, 1 Drawing Sheet

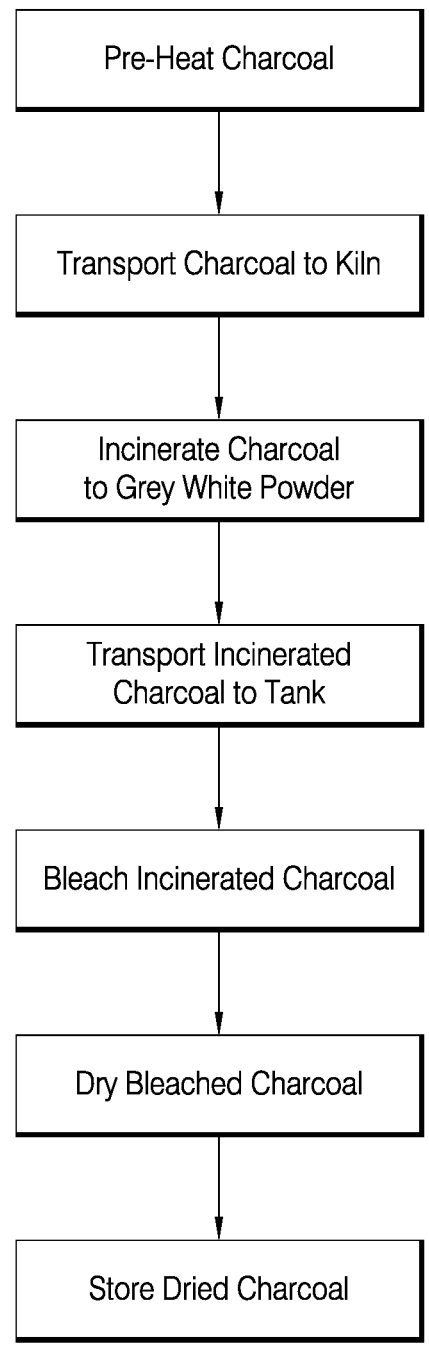

WHITE CHARCOAL TOOTHPASTE COMPOSITION AND METHOD

CROSS REFERENCE TO RELATED APPLICATIONS

The present application claims the benefit of U.S. Provisional Application 62/630,033 filed Feb. 13, 2018.

FIELD OF THE INVENTION

The field of the present invention generally relates to whitening toothpaste and related oral care products.

BACKGROUND OF THE INVENTION

Some might find the choice of toothpaste to be an unremarkable decision made at one or both sleepy times of our busy day, but in fact there have been great advances in this field of technology time and again. For two well-known examples, consider the introduction of fluoride salts and of artificial sweeteners—the first introduced an active technology to fight cavity formation and growth by artificially replacing enamel on teeth and the second drastically improved the frequency and consistency of brushing— merely by improving the brushing experience without the use of natural sugars (which are known to feed cavity-forming bacteria and fuel plaque formation).

Black activated charcoal has only recently become a popular ingredient in oral care products. Even as more products using black activated charcoal have been introduced into the market, it has been found that black activated charcoal is very messy and inconvenient. It blackens the brusher's mouth and can leave unsightly stains on toothbrushes, bathroom sinks, mirrors and floors. The present invention addresses these and other problems with the prior art by presenting a method for transforming activated charcoal (typically dark-grey-to-black in appearance) into a white activated charcoal (white-to-light-grey in appearance) via high temperatures and bleaching with hydrogen peroxide. In a further embodiment, other novel ingredients are compounded with the white activated charcoal, resulting in a more natural and superior toothpaste product than has previously been produced using the prior art. The embodiments of the present invention—methods and compositions—work to make the entire process of using activated charcoal to whiten the brusher's teeth more easy, pleasant and effective.

Novel inventions can be highly effective and yet still struggle to break through into widespread use. Sometimes an invention relies on a new and unfamiliar technology that raises concerns about safety (such as the introduction of air travel) or has unproven efficacy (such as the introduction of new surgical implant device). Activated charcoal is a very old technology, providing a unique adsorbant profile in the micro pitting—known to attract and retain (i.e. adsorb) a variety of contaminants—ranging from staining materials to microbes. Active charcoal has been successfully added to toothpaste as a whitening agent. Despite the impressive research demonstrating an efficacy which rivals that of chemical bleaching agents, harsh and often toxic chemical bleaching agents remain the typical consumer's preferred choice of whitener.

The present invention offers an optically white activated charcoal which behaves no differently from the more familiar black form. Because there is widespread suspicion of chemical additives and a growing demand for safe and natural alternatives, the present invention takes a novel approach and has the potential to transform dental care in a manner similar to that of fluoride by breaking through reluctant consumer uptake of a highly effective product, which has previously been dirty and messy to use.

The present invention introduces the application of optically white activated charcoal to replace the familiar activated charcoal (with dark appearance) known in prior art— to whiten teeth naturally without the mess. One further embodiment of the present invention sets forth a simple yet novel process for producing whited activated charcoal toothpaste. A further embodiment formulates a complete toothpaste solution based on activated white charcoal yielding, remarkable whitening with a formula that provides a familiar dental toothpaste experience while avoiding the use of harsh chemical additives and common allergens.

SUMMARY OF THE INVENTION

A method for producing white activated charcoal (activated charcoal with a white-to-light-grey appearance) is disclosed. Furthermore, oral care compositions (toothpaste, mouth rinse, teeth whitening gel or other oral hygiene products) containing white activated charcoal are disclosed. In particular, a novel formulation of whitening toothpaste featuring white activated charcoal (activated charcoal with a white-to-light-grey appearance) is disclosed. In a further embodiment, white activated charcoal is combined with one or more additional ingredients in a simple toothpaste providing excellent whitening. Finally, in a preferred further embodiment, the white activated charcoal is compounded into a complete toothpaste formula providing both excellent whitening action and drastically improved oral health.

According to the present invention a white activated charcoal toothpaste is made by first preparing the white charcoal, and then compounding the white charcoal with a variety of ingredients, as shown in the accompanying Table 1, to create a final white charcoal toothpaste.

The method for creating white charcoal employs a pre-heater, a kiln (for example a rotary kiln), a cooler and a bleaching chamber. Black activated charcoal is first heated in a preheater to approximately 600° F., and is then moved to the rotary kiln for final heating to a white-hot state (approximately 1400° F.). The newly whitened charcoal is quickly transferred to a cooler and brought down to room temperature. When the whitened charcoal returns to room temperature it is moved to a stainless-steel chamber where it is submersed in a solution of 50% hydrogen peroxide. The wet white charcoal is returned to the pre-heater for final drying. In a preferred embodiment the charcoal is passed through a US Mesh 70 sieve, and particle sizes will range from 0.1 mm to 0.5 mm with a size predominantly less than 0.21mm. It should be understood that the white activated charcoal can now be used and added to a variety of traditional oral care products, including traditional toothpaste and oral rinse formulas.

In one preferred embodiment of the invention, a toothpaste minimally including white activated charcoal is compounded in a solvent base (e.g. water).

In a further preferred embodiment of the invention, a toothpaste minimally including white activated charcoal and a dental abrasive (e.g. Hydrated Silica Sident® 9) is compounded in a solvent base (e.g. water).

In a further preferred embodiment, one or more of the following ingredients are compounded in a solvent base along with white activated charcoal and a dental abrasive: one or more thickening agents (e.g. Hydrated Silica Sident®

22s and/or irish moss), a humectant (e.g. glycerin), a surface active agent (i.e. a foaming agent) (e.g. sodium coco sulfate), a protective surface polish (e.g. jojoba wax oil), and an extrinsic stain removal agent (e.g. calcium peroxide).

In a further embodiment still, and in order to improve the user experience and encourage consumer uptake of the invention, additional ingredients can be added to provide a more common look, feel, mouthfeel, taste and flavor, including, for example, one or more of sweeteners, flavorings or colorants. In one particular embodiment xylitol can be added as a sweetener. In another embodiment, peppermint oil or another aromatic essential oil can be added as a flavoring. In yet another embodiment, titanium dioxide can be added as a white colorant to give the toothpaste the white appearance of a more typical paste. Table 1 set forth below gives ingredient functions for certain preferred ingredients. In another embodiment, a fluoride ingredient can be added to any of the foregoing compositions.

TABLE 1

| Ingredient Function | Preferred Ingredients |
| --- | --- |
| White Activated Charcoal for dental whitening (via extrinsic stain removal) & breath freshening (via adsorbance of odor causing surface bacteria) | White Activated Charcoal (white-to-light-grey) |
| Dental abrasive (tooth cleaning abrasive) | Hydrated Silica (Sident® 9) |
| Solvent base (to dissolve other ingredients) | Aqua (water) |
| Primary thickening agent | Hydrated Silica (Sident® 22s) |
| Humectant | Glycerin |
| Surface active agent (foaming agent) | Sodium Coco Sulfate |
| Protective surface polish | Jojoba Wax Oil |
| Chemical whitener (secondary extrinsic stain removal agent) | Calcium Peroxide |
| Secondary Thickening Agent | Irish Moss |
| Sweetener | Glycerin or Xylitol |
| Flavoring | Peppermint |
| Colorant | Titanium Dioxide |
| Fluoride | Anticavity |

Dental abrasives are well known in the art. Silica dental abrasives, of various types, can provide the unique benefits of exceptional dental cleaning and polishing performance without unduly abrading tooth enamel or dentin. Silica abrasive materials are also exceptionally compatible with sources of soluble fluoride and other optional ingredients. For these reasons they are preferred for use herein. The silica abrasives used in the present invention generally have an average particle size ranging between about 0.1 to 30 microns, preferably 5 and 15 microns. The silica abrasive can be precipitated silica powders or silica gels such as the silica xerogels described in Pader et al, U.S. Pat. No. 3,538,230, issued Mar. 2, 1970 and DiGiulio, U.S. Pat. No. 3,862,307, Jun. 21, 1975, both incorporated herein by reference.

The toothpaste of the present invention comprises pastes and gels that are thickened with silica such as, for example, a mixture of viscosing silica and abrasive silica. Such a toothpaste contains, in addition to water, at least two abrasive silicas including one abrasive silica, preferably Sident® 9 and a softer thickening silica, namely Sident® 22s. SIDENT® 22 S is a fine particle silica with high oil absorption (DBP) and medium to high thickening effect in liquids. It is very fine and provides little abrasion. SIDENT® 9 is a medium particle silica with high hardness and low to medium thickening effect in liquids.

Other possible abrasives can be used instead of or in addition to the preferred abrasive system described above, depending on the degree of abrasion desired and should be obvious to anyone skilled in the art of toothpaste formulation. These include other synthetic abrasive polishing agents such as "Zeodent" or with amorphous precipitated silicas and pre-mixed silica gels. Other abrasive agents include calcium carbonate, magnesium carbonate, sodium metaphosphate, potassium metaphosphate, zirconium silicate, potassium metaphosphate, magnesium orthophosphate, tricalcium phosphate, magnesium orthophosphate, trimagnesium phosphate, aluminum silicate, zirconium silicate and perlite.

The delivery vehicle (solvent base) is preferably aqueous, but it is within the broader scope of the invention to employ non-aqueous vehicles. Generally the liquid will contain a humectant or other viscous water-miscible material such as glycerin, sorbitol, polyethylene glycol, mannitol or mixtures thereof. When water is present it preferably constitutes about 5 to 35% (e.g. about 10 to 30%) of the total vehicle. Superior results (such as better taste) are obtained when the proportion of water is relatively low, e.g. about 10 to 20% of the total toothpaste, such as when the water to glycerin ratio is in the range of about 0.4:1 to 0.7:1.

Gel toothpastes generally contain up to 8.5% by weight thickening silica whereas opaque toothpastes typically contain 3 to 4% by weight thickening silica. Certain preferred embodiments of toothpaste compositions may include up to 2% by weight thickening silica. Further preferred compositions have 1.5% by weight, or even less than 1% by weight thickening silica. Optimal compositions may have less than 0.5% by weight thickening silica. Certain highly preferred compositions are free of thickening silica. When present, preferred thickening silicas include silica gels such as the SYLODENT® or SIDENT® series from W. R. Grace & Co or precipitated silica such as ZEOTHIX® 265 from J. M. Huber Corporation. AEROSIL® T series from Degussa or the CAB-O-SIL® series from Cabot Corporation may also be used as well as any similar toothpaste silica. Other useful silica thickeners also include ZEODENT® 165, ZEODENT® 163 and/or 167 and ZEOFREE® 153, 177, and/or 265 silicas, all available from J. M. Huber Corporation. Other preferred thickening silicas include MFIL®, MFIL®-P (From Madhu Silica, India), SIDENT® 22 S and AEROSIL® 200 (Ex. Evonik Industries), SYLODENT® and SIDENT® thickening silicas from WR Grace & Company and Tixosil® 43 and 331 from Rhodia.

A gelling agent for toothpaste vehicles is well known in the art. These are often high polymers (e.g. gums or other thickening agents) which are soluble or swellable in water or other aqueous medium. For example, sodium carboxymethylcellulose has given excellent results. Other materials are hydrated gum tragacanth, gum arabic, gum karaya, sodium alginate, hydroxyethyl cellulose, methyl cellulose, ethyl cellulose, carrageen and other polysaccharides, polyvinyl pyrollidones or such thickening agents as "Veegum" (a complex magnesium aluminum silicate). The amount of thickening agent used in a preferred embodiment is preferably sufficient to impart to the mixture the pasty consistency, body and the non-tacky nature which is characteristic of conventional dental creams or toothpastes. As is known in the art, such dental creams are extrudable from ordinary collapsible toothpaste tubes to form a ribbon of substantial thickness (e.g. about ⅜ inch) which if left undisturbed, substantially retains its original thickness over a period of say, one minute or more (and does not penetrate substantially into the bristles of a toothbrush when resting on the end of such bristles for a similar period); but which preferably offers no substantial resistance to brushing or to deformation when, for instance, one touches it lightly with a finger; and which has little tack, in that it does not tend to form a string when the finger is pulled away from the ribbon. The proportion of thickening agent is often within the range of about 0.5 to 2% by weight, such as about 0.8 to 1.5% by weight, of the toothpaste.

An organic surface active agent is preferably used in the compositions of the present invention to aid in the prophylactic action in the thorough dispersion of the composition throughout the oral cavity, and to improve cosmetic acceptability and detersive and foaming properties. Among these are water-soluble salts of the higher alkyl sulfates, such as sodium lauryl sulfate or other suitable alkyl sulfate having 8 to 18 carbon atoms in the alkyl group; water-soluble salts of sulfonated monoglycerides of higher fatty acids such as sodium coconut monoglyceride sulfonate or other suitable sulfonated monoglyceride of a fatty acid of 10 to 18 carbon atoms; salts of amides of higher fatty acid (e.g. 12 to 16 carbon atom acids) with lower aliphatic amino acids (e.g. taurine or sarcosine) or other amino acid of 2 to 6 carbon atoms, such as sodium-N-methyl-N-palmitoyl tauride, sodium N-lauroyl, N-myristoyl or N-palmitoyl sarcosinates; water-soluble salt of the esters of such fatty acids with isethionic acid or with glycerol monosulfate, such as the sodium salt of the monosulfated monoglyceride of hydrogenated coconut oil fatty acids; water-soluble salts of olefin sulfonates, e.g. alkene sulfonates or hydroxyalkane sulfonates or mixtures thereof having 12 to 18 carbon atoms in the carbon chain of the molecule; water-soluble soaps of higher fatty acids such as those of 12-18 carbon atoms (e.g. coconut fatty acids). The cation of the salt may be, for instance, sodium (which is preferred) potassium or mono-di- or triethanolamine. Mixtures of surface active agents may be used. In an embodiment, a particularly suitable mixture which provides a high foaming powder with little or no irritating effect comprises a higher alkyl sulfate and a higher fatty acid sarcosinate, e.g. in a ratio of about 1:2 to 2:1, such as about 1:1; instead of all or part of the sarcosinate, a higher fatty acid monoglyceride sulfonate may be present.

Other suitable surface-active materials include nonionic agents such as condensates of sorbitan monostearate conjugated with ethylene oxide (e.g. Polysorbate 60), condensates of ethylene oxide with propylene oxide, condensates of propylene glycol (available under the trademark "Pluronics"), and amphoteric agents such as quaternized imidazole derivatives which are available under the trademark "Miranol" such as Miranol C2 M. Cationic surface-active germicides and antibacterial compounds may also be used. Such compounds include di-isobutylphenoxyethyoxyethyl dimethyl benzyl ammonium chloride, benzyl dimethyl stearyl ammonium chloride, tertiary amines, having one fatty alkyl group (of from 12 to 18 carbon atoms) and two (poly) oxyethylene groups attached to the nitrogen (typically containing a total of from about 2 to 50 ethenoxy groups per molecule) and salts thereof with acids, and organic compounds that contain a side chain of at least one (1) fatty alkyl group consisting from about 12 to 18 carbon atoms, and x, y and z total 3 or higher, as well as salts thereof with mineral or organic acids. It is preferred to use from about 0.05 to 5% by weight of the foregoing surface-active materials in the instant dentifrice preparations. The proportion of surface-active agent is preferably within the range of about 0.1 to 10% of the toothpaste, more preferably in the range of about 1 to 3% by weight, such as about 1.5 to 2% by weight.

A protective surface polish may be used such as jojoba wax oil, which increases enamel luster and shine (increasing white light reflectance) and creates a slick surface (repelling new stains and discolorations from depositing).

A chemical whitener, or extrinsic stain remover, may be used such as calcium peroxide. Calcium peroxide is a mineral-like powder. It is hard and has the ability to clean teeth through abrasion. Calcium peroxide also releases oxygen free radicals, when it is abraded, and these free radicals can oxidize colored chromagens and change their color to clear, thus reducing the visible stains and whitening teeth.

A secondary thickening agent may be used such as irish moss, iota-carrageenan, kappa-carrageenan, gum tragacanth, starch, polyvinylpyrrolidone, hydroxyethyl propyl cellulose, hydroxybutyl methyl cellulose, hydroxypropyl methyl cellulose, hydroxyethyl cellulose and sodium carboxymethyl cellulose or any combination thereof.

Any suitable flavoring or sweetening materials may be employed in formulating a flavor for the compositions of the present invention. Examples of suitable flavoring constituents include the flavoring oils, for example, oils of spearmint, peppermint, wintergreen, sassafras, clove, sage, eucalyptus, marjoram, cinnamon, lemon and orange, as well as methylsalicylate. Suitable sweetening agents include xylitol, lactose, maltose, sorbitol, sodium cyclamate, perillartine, saccharine and ammoniated glycyrrhizin (e.g. monoammonium salt). Suitably, flavor and sweetening agent together comprise from about 0.01 to 50 percent or more of the compositions of the various embodiments of the instant invention. Preferably the amount of flavoring oil is above 0.4% by weight (e.g. 0.81 to 5% by weight).

Colorants, such as titanium dioxide, are well known in the art. The weight of titanium dioxide ($TiO_2$) particles in the toothpaste is generally above about 0.9% by weight. The amount of $TiO_2$ is included in amounts up to about 6.0%, preferably about 0.2 to 6.0% by weight of the toothpaste. The particle size of the $TiO_2$ is preferably about 0.1 to 1 micron. The addition of $TiO_2$ gives the toothpaste a white color, making the gel appear more like a paste.

Table 2 set forth below shows the minimal and preferred ranges of possible ingredient percentage (%) by weight of a complete toothpaste compound offering whitening, polishing and cleansing in various embodiments of the present invention.

TABLE 2

| Formula | Minimal Range (% by wt) | Preferred Range (% by wt) |
|---|---|---|
| White activated charcoal | 0.1% to 60% | 0.1% to 60% |
| Dental abrasive | 2% to 25% | 2% to 25% |
| Solvent base | 10% to 60% | 10% to 60% |
| Primary thickening agent | 0% to 20% | 2% to 20% |
| Humectant | 0% to 60% | 10% to 60% |
| Surface active agent | 0% to 10% | 0.1% to 10% |
| Protective surface polish | 0% to 10% | 0.1% to 10% |
| Chemical whitener | 0% to 50% | 0.1% to 50% |
| Secondary thickening agent | 0% to 10% | 0.5% to 10% |
| Sweetener | 0% to 50% | 0.5% to 50% |
| Flavoring | 0% to 5% | 0.1% to 5% |
| Colorant | 0% to 6% | 0.2% to 6% |
| Fluoride | 0% to 3% | 0.1% to 3% |

BRIEF DESCRIPTION OF THE DRAWINGS

Preferred and alternative examples of the present invention are described in detail below with reference to the following Figure drawing:

FIG. 1 is a process flow diagram showing a process by which white activated charcoal is prepared.

DETAILED DESCRIPTION

The invention shown in FIG. 1 is a preferred process by which white activated charcoal is prepared for compounding into a white activated charcoal toothpaste.

First, black charcoal derived from birch trees is Preheated to 600° F. in an RTC Model SMD-624B IR Reflow Furnace. Second, heated charcoal is transported at slow speed to a kiln via conveyor. Third, heated charcoal is incinerated to a grey white powder by heating it to 1600° F. in an HTT Rotary Kiln Model 500RKILN-SW-AB-G. Fourth, hot incinerated charcoal is transported to a tank at slow speed via a Titan Model 630 Cooling and Drying Conveyor. Fifth, cooled incinerated charcoal is bleached by mixing it with 35% Hydrogen Peroxide while cooling to 68° F. at a mixing speed of 5 rpm +/−2 rpm in an Indco 1500 Gallon Stainless Steel Mixing Tank. Sixth, the bleached wet white charcoal is dried at high fan and slow speed via a Titan Model 630 Cooling and Drying Conveyor. Lastly, dried white charcoal is stored in air tight conditions in an Indco 1500 Gallon Stainless Steel Mixing Tank.

The embodiments of the invention in which an exclusive property or privilege is claimed are defined as follows:

1. A method for preparing a white activated charcoal, comprising: subjecting a charcoal ingredient to an incineration step and a bleaching step.

2. The method according to claim 1, wherein the charcoal ingredient is derived from birch trees.

3. The method according to claim 1, further comprising: a pre-heating step.

4. The method according to claim 1, further comprising: a drying step.

5. An oral care composition comprising: a white activated charcoal.

6. The oral care composition according to claim 5, further comprising a solvent base.

7. The oral care composition according to claim 6, further comprising a dental abrasive.

8. The oral care composition according to claim 7, wherein the dental abrasive is hydrated silica.

9. A toothpaste composition comprising: (a) from 0.1% to 60% by weight of a white activated charcoal; (b) from about 2.0% to 25.0% by weight of a dental abrasive; (c) from about 10% to 60% of a solvent base, wherein the percentage by weight is relative to the total weight of the composition, and wherein the composition is for cleansing teeth.

10. The oral care composition according to claim 7, further comprising a humectant.

11. The oral care composition according to claim 10, wherein the humectant is glycerin.

12. The toothpaste composition according to claim 9, further comprising from about 10% to 60% by weight of a humectant, wherein the percentage by weight is relative to the total weight of the composition.

13. The oral care composition according to claim 7, further comprising a thickener.

14. The oral care composition according to claim 13, wherein the thickener is hydrated silica.

15. The toothpaste composition according to claim 9, further comprising from about 2.0% to 20% by weight of a thickener, wherein the percentage by weight is relative to the total weight of the composition.

16. The toothpaste composition according to claim 15, further comprising from about 0.5% to 10% by weight of a second thickener, wherein the percentage by weight is relative to the total weight of the composition.

17. The oral care composition according to claim 7, further comprising a surface active agent.

18. The oral care composition according to claim 17, wherein the surface active agent is sodium coco sulfate.

19. The toothpaste composition according to claim 9, further comprising from about 0.1% to 10% by weight of a surface active agent, wherein the percentage by weight is relative to the total weight of the composition.

20. The oral care composition according to claim 7, further comprising an extrinsic stain remover.

21. The oral care composition according to claim 20, wherein the extrinsic stain remover is calcium peroxide.

22. The toothpaste composition according to claim 9, further comprising from about 0.1% to 50% by weight of an extrinsic stain remover, wherein the percentage by weight is relative to the total weight of the composition.

23. The oral care composition according to claim 7, further comprising a protective surface polish.

24. The oral care composition according to claim 23, wherein the protective surface polish is jojoba wax oil.

25. The toothpaste composition according to claim 9, further comprising from about 0.1% to 10% by weight of a protective surface polish, wherein the percentage by weight is relative to the total weight of the composition.

26. The oral care composition according to claim 7, further comprising a sweetener.

27. The oral care composition according to claim 26, wherein the sweetener is xylitol.

28. The toothpaste composition according to claim 9, further comprising from about 0.5% to 50% by weight of a sweetener, wherein the percentage by weight is relative to the total weight of the composition.

29. The oral care composition according to claim 7, further comprising a flavoring.

30. The oral care composition according to claim 29, wherein the flavoring is an aromatic essential oil.

31. The oral care composition according to claim 29, wherein the flavoring is peppermint oil.

32. The toothpaste composition according to claim 9, further comprising from about 0.1% to 5.0% by weight of a flavoring, wherein the percentage by weight is relative to the total weight of the composition.

33. The oral care composition according to claim 7, further comprising a colorant.

34. The oral care composition according to claim 33, wherein the colorant is titanium dioxide.

35. The toothpaste composition according to claim 9, further comprising from about 0.2% to 6.0% by weight of a colorant, wherein the percentage by weight is relative to the total weight of the composition.

* * * * *